US010064892B2

(12) United States Patent
De Groot-Barrere et al.

(10) Patent No.: US 10,064,892 B2
(45) Date of Patent: Sep. 4, 2018

(54) METHOD FOR PRODUCING AN OSTEOINDUCTIVE CALCIUM PHOSPHATE AND PRODUCTS THUS OBTAINED (71) Applicant: KUROS BIOSCIENCES B.V., Bilthoven (NL)

(72) Inventors: Florence De Groot-Barrere, Bilthoven (NL); Vincent Van Miegem, Bilthoven (NL); Huipin Yuan, Bilthoven (NL); Joost De Bruijn, Bilthoven (NL)

(73) Assignee: KUROS BIOSCIENCES B.V., Bilthoven (NL)

( * ) Notice: Subject to any disclaimer, the term of this patent is extended or adjusted under 35 U.S.C. 154(b) by 0 days.

(21) Appl. No.: 14/904,676

(22) PCT Filed: Jul. 18, 2014

(86) PCT No.: PCT/NL2014/050491
§ 371 (c)(1),
(2) Date: Jan. 12, 2016

(87) PCT Pub. No.: WO2015/009154
PCT Pub. Date: Jan. 22, 2015

(65) Prior Publication Data
US 2016/0166610 A1 Jun. 16, 2016

(30) Foreign Application Priority Data
Jul. 18, 2013 (NL) ..................................... 2011195

(51) Int. Cl.
A61L 27/32 (2006.01)
A61L 27/56 (2006.01)
A61K 33/42 (2006.01)
A61L 27/12 (2006.01)
A61K 9/14 (2006.01)

(52) U.S. Cl.
CPC ............... *A61K 33/42* (2013.01); *A61K 9/14* (2013.01); *A61L 27/12* (2013.01); *A61L 27/32* (2013.01); *A61L 27/56* (2013.01); *A61L 2400/12* (2013.01); *A61L 2400/18* (2013.01); *A61L 2430/02* (2013.01)

(58) Field of Classification Search
CPC .................................. A61L 27/12; A61L 27/56
See application file for complete search history.

(56) References Cited

U.S. PATENT DOCUMENTS

| 5,141,576 | A | * | 8/1992 | Shimamune | A61F 2/30767 |
| | | | | | 148/254 |
| 5,185,177 | A | | 2/1993 | Kijima et al. | |
| 6,338,810 | B1 | | 1/2002 | Carpena et al. | |
| 6,511,510 | B1 | | 1/2003 | De Bruijn et al. | |
| 7,501,179 | B2 | | 3/2009 | Song et al. | |
| 7,749,429 | B2 | | 7/2010 | Furuzono et al. | |
| 7,942,934 | B2 | | 5/2011 | Yuan et al. | |
| 7,947,368 | B2 | | 5/2011 | Song | |
| 8,025,676 | B2 | | 9/2011 | Buchanan | |
| 8,029,755 | B2 | | 10/2011 | Ahn | |
| 8,153,255 | B2 | | 4/2012 | Furuzono et al. | |
| 8,597,604 | B2 | | 12/2013 | Ahn | |
| 8,734,524 | B2 | | 5/2014 | Bufler | |
| 8,734,835 | B2 | | 5/2014 | McKay et al. | |
| 9,066,995 | B2 | | 6/2015 | Bufler | |
| 9,211,359 | B2 | | 12/2015 | McKay et al. | |
| 9,272,072 | B1 | | 3/2016 | Ismailoglu et al. | |
| 2002/0035402 | A1 | | 3/2002 | de Bruijn et al. | |
| 2008/0031914 | A1 | | 2/2008 | Drapeau et al. | |
| 2010/0041770 | A1 | | 2/2010 | Liu et al. | |
| 2011/0020419 | A1 | | 1/2011 | Yuan et al. | |
| 2012/0021008 | A1 | | 1/2012 | De Bruijn et al. | |

FOREIGN PATENT DOCUMENTS

| CN | 102515849 | 6/2012 |
| EP | 0 915 684 | 5/1999 |
| EP | 0 947 489 | 10/1999 |
| EP | 0 987 032 | 3/2000 |
| EP | 1 718 346 | 11/2006 |
| EP | 1 808 411 | 7/2007 |
| EP | 1 963 386 | 9/2008 |
| EP | 1 993 624 | 11/2008 |
| EP | 2 001 527 | 12/2008 |
| EP | 2 296 720 | 3/2011 |
| EP | 2 301 591 | 3/2011 |
| EP | 2 320 961 | 5/2011 |

(Continued)

OTHER PUBLICATIONS

Yubao, L. et al. "Morphology and composition of nanograde calcium phosphate needle-like crystals formed by simple hydrothermal trreatment", J Mat Sci Med. (1994) 5:326-331.*

Arinzeh, T. et al., "A comparative study of biphasic calcium phosphate ceramics for human mesenchymal stem-cell-induced bone formation", Biomater (2005) 26:3631-3638.*

Brown, O et al., "Sintering of biphasic calcium phosphates", J Mater Sci Mater Med (2010) 21:2271-2279.*

(Continued)

*Primary Examiner* — Gina C Justice (74) *Attorney, Agent, or Firm* — Morrison & Foerster LLP (57) ABSTRACT

The invention relates to a method for producing an osteoinductive calcium phosphate material, the method comprising the steps of providing a sintered calcium phosphate starting material having a surface topography consisting of calcium phosphate grains, subjecting the sintered calcium phosphate starting material to a hydrothermal treatment of between 125-150° C. for a duration sufficient to change calcium phosphate grains on the surface of the starting material into calcium phosphate needles.

8 Claims, 6 Drawing Sheets

(56) References Cited

FOREIGN PATENT DOCUMENTS

| EP | 2 445 543 | 5/2012 |
|----|-----------|--------|
| WO | WO-2010/149296 | 12/2010 |
| WO | WO 2011/009635 | 1/2011 |
| WO | WO 2012/084214 | 6/2012 |

OTHER PUBLICATIONS

International Search Report for PCT/NL2014/050491, dated Oct. 2, 2014, 3 pages.

* cited by examiner

METHOD FOR PRODUCING AN OSTEOINDUCTIVE CALCIUM PHOSPHATE AND PRODUCTS THUS OBTAINED

CROSS-REFERENCE TO RELATED APPLICATIONS

This application is the national phase of PCT application PCT/NL2014/050491 having an international filing date of 18 Jul. 2014, which claims benefit of Dutch patent application No. 2011195 filed 18 Jul. 2013. The contents of the above patent applications are incorporated by reference herein in their entirety.

FIELD OF THE INVENTION

The invention relates to a surface treatment for calcium phosphates used as bone graft material in regenerative medicine, and to osteoinductive calcium phosphates obtained by such treatments.

BACKGROUND OF THE INVENTION

Synthetic bone substitutes must be biocompatible, osteoconductive, and mechanically compatible with native bone in order to be successfully used in clinical settings. Further improvement of the material is achieved by more rapid bone ingrowth and even stimulation of bone forming capacity of the body, or bone induction. This property of the implant material refers to its capacity to induce osteogenesis, or the mechanism that triggers stem cells to differentiate into bone-forming osteoblasts.

Osteoinduction is reported primarily for a subgroup of calcium phosphate ceramics, including hydroxyapatite (HA), β-tricalcium phosphate (β-TCP), biphasic calcium phosphate (BCP), that designates the mixture of HA and TCP, dicalcium phosphate anhydrous (DCPA), dicalcium phosphate dihydrate (DCPD), carbonated apatite, calcium pyrophosphates (CPP) and HA/calcium carbonate (CC) mixtures. Despite a thorough analysis of the materials described so far as osteoinductive, it is still not possible to describe how exactly an osteoinductive material should be designed and produced. All that is clear is that osteoinductive capacity can best be determined by heterotopic implantation, i.e. implantation in the tissues or organs where bone does not naturally grow, such as by ectopic implantation (i.e. intramuscular implantation or subcutaneous implantation).

In general, certain porous calcium phosphates have been found to exhibit osteoinductivity. For instance, Yamasaki et al., in Biomaterials 13:308-312 (1992), describe the occurrence of heterotopic ossification (formation of new bone in tissue that does not normally ossify) around porous hydroxyapatite ceramic granules, but not around dense granules. The porous granules range in size from 200 to 600 µm, and have a continuous and interconnected microporosity of which the pores range in diameter from 2 to 10 µm.

U.S. Pat. No. 6,511,510 describes a biocompatible and biodegradable calcium phosphate that exhibits improved osteoinductivity over the porous hydroxyapatite granules of Yamasaki et al. The biodegradable calcium phosphate has a total porosity of 20 to 90%, and encompasses both macropores ranging in size from 0.05 to 1.5 mm, as well as micropores ranging in size from 0.05 to 20 µm. The biodegradable calcium phosphate material is produced by mould casting and blocks can subsequently be granulated or cut to smaller size particles. The material, when implanted, is suitable to function as a (temporary) substitute for bone.

Despite the availability of the above materials, it would be advantageous if biomaterials for use in connection with living tissues could be provided with even better osteoconductive and osteoinductive properties, i.e. that result in even faster and more profound bone formation. It would also be advantageous if such osteoinductive materials could be easily introduced in the body of the mammal, most preferably such that they provide an easily implantable and effective scaffold material for the production of new bone in both osseous and non-osseous sites. Such material would be of much use for the production of de novo autologous bone, which might subsequently be used as bone substitute for repairing large bone defects.

SUMMARY OF THE INVENTION

The present invention provides a calcium phosphate material having excellent osteoinductive properties.

In particular, the present invention provides a method for treating calcium phosphates, in particular sintered calcium phosphates, which treatment method renders the material, and in particular its surface, more osteoinductive relative to an untreated material.

The present invention now provides a method for producing an osteoinductive calcium phosphate material, the method comprising the steps of providing a sintered biphasic calcium phosphate (BCP) starting material having a surface topography consisting of calcium phosphate grains, subjecting the sintered biphasic calcium phosphate starting material to a hydrothermal treatment at a temperature equal to or higher than 125° C. for a duration sufficient to change calcium phosphate grains on the surface of the starting material into calcium phosphate needles.

In a preferred embodiment of a method of the invention, the BCP starting material prior to the hydrothermal treatment comprises an amount of 4-20% of apatite. More preferably, the apatite is a hydroxyapatite.

In another preferred embodiment of a method of the invention, the calcium phosphate starting material prior to the hydrothermal treatment has an average grain size in a range of 0.1-3.0 µm, more preferably 0.2-2.5 µm, more preferably the median grain size is about 0.5-2.2 µm, 0.75-1.5 µm.

It is a preferred feature of the pre- and post-treatment material that it is porous.

It is another preferred feature of the pre- and post-treatment material that it exhibits macroporosity (pores ranging in size from 0.1 to 1.5 mm).

The hydrothermal treatment changes the calcium phosphate grains on the surface of the starting material into calcium phosphate needles. The change in surface topography from a grain-like to a needle-like topography is associated with an increase in specific surface area and total pore area, consequently the surface protein adsorption capacity increases considerably due to the hydrothermal treatment as described herein.

In a preferred embodiment of a method of the invention, the total pore area of the calcium phosphate starting material will increase by at least 10-65% following the hydrothermal treatment as compared to an untreated control material. The total pore area may be measured by mercury intrusion and expressed in $m^2/g$.

In still another preferred embodiment of a method of the invention, the total pore area of the calcium phosphate starting material will increase by at least 100% following the hydrothermal treatment as compared to an untreated control material.

In still another preferred embodiment of a method of the invention, the protein adsorption capacity of the calcium phosphate starting material increases by at least 10-50% following the hydrothermal treatment as compared to an untreated control material. The protein adsorption capacity may be determined by the determining the amount of serum proteins or albumin adsorbed after incubation at 37° C. and measuring the amount of protein remaining in solution following an incubation with a predetermined amount of the calcium phosphate material for a predetermined time period. Proteins can be measured spectrophotometrically using for instance a bicinchoninic acid (BCA) assay.

In still another preferred embodiment of a method of the invention, the protein adsorption capacity of the calcium phosphate starting material increases by at least 50% following hydrothermal treatment as compared to an untreated control material.

The present invention in another aspect provides an osteoinductive calcium phosphate material, obtainable by a method according to the invention as described above. Such an osteoinductive calcium phosphate preferably has a protein adsorption capacity that is at least 40% higher than a comparative untreated starting material. This increased protein adsorption capacity is believed to be associated with the increase in specific surface area resulting from the treatment. In fact, the treatment may double the specific surface area of the calcium phosphate material.

A osteoinductive calcium phosphate material of the present invention having needle-like surface topography, such as may for instance be obtained by a method as described above, has a specific surface area as well as a total pore area that are larger than a reference material of similar composition but comprising a grain-like surface topography. In particular, an improved osteoinductive material of the invention has a total pore area of preferably at least 1.8 $m^2/g$. More preferably, the improved osteoinductive material of the invention has a total pore area of at least 1.85 $m^2/g$, more preferably at least 1.9 $m^2/g$, even more preferably at least 2.0 $m^2/g$, more preferably more than 2.5, 2.8, 3.0, 3.5, 4.0 or 4.5 $m^2/g$ as determined by mercury intrusion. In particular, an improved osteoinductive material of the invention has a specific surface area of preferably at least 0.7 $m^2/g$. More preferably, the improved osteoinductive material of the invention has a specific surface area of more than 0.9 $m^2/g$, more preferably more than 1.0, 1.5, 2.0, 2.5 or 3.0 $m^2/g$ as determined by BET.

An osteoinductive calcium phosphate material of the present invention having needle-like surface topography, such as may for instance be obtained by a method as described above, has a protein adsorption capacity that is larger than a reference material of similar composition but comprising a grain-like surface topography. In particular, an improved osteoinductive material of the invention has a protein adsorption capacity of preferably at least 1.0-3.0 mg of serum proteins per cc of material (from 2 ml of 1% FBS), or at least 1000-3500 µg of BSA per cc of material (from 2 ml of 400 µg/ml BSA).

The osteoinductive calcium phosphate material obtainable by methods of this invention may have a higher or lower amount of hydroxyapatite than the starting calcium phosphate material, preferably higher. A biphasic calcium phosphate starting material comprising an amount of 10% of hydroxyapatite, may exhibit an amount of higher than 30% hydroxyapatite following the hydrothermal treatment.

An osteoinductive calcium phosphate material obtained by a method of the present invention is in a preferred embodiment a biphasic calcium phosphate (BCP) ceramic, preferably comprising 5 to 65%, such as 50%, of hydroxyapatite (HA), and 35 to 95%, such as 50%, of β-tricalcium phosphate (β-TCP).

The osteoinductive calcium phosphate material obtained by a method of the present invention has needle-like surface topography. The size of these needles is typically 10-1500 nm in diameter. The material is furthermore preferably porous.

The material produced by methods of the invention exhibits excellent osteoinductive behaviour in living tissue, primarily due to its outstanding protein adsorption capacity. The formation of bone tissue at the surface of the material of the invention assists in a favourable acceptation of an implant made of said material. Moreover, the formation of bone tissue accelerates the recovery of any damage in the bone structure, which forms the reason for applying the implant.

An osteoinductive calcium phosphate of the invention is preferably in the form of microparticles having a particle size ranging from about 50 to about 1500 µm, more preferably from about 200 to about 500 µm, most preferably 212-300 µm. In alternative embodiments, the calcium phosphate of the invention is preferably in the form of granules having a granule size range of preferably 1000-4000 µm. In another alternative embodiment, the calcium phosphate of the invention is in the shape of a block of several cubic centimeters (e.g. 0.5, 1, 1.5, 2, 2.5, 3 $cm^3$), a block that is pre-shaped, or a block that can be shaped to the size of a (bone) defect by a scalpel or burr.

The osteoinductive calcium phosphate ceramic of the present invention typically has a total pore area that is 0.5, 1, 1.5, 2, 2.5 or even 3 times higher than that of the corresponding calcium phosphate ceramic starting material prior to the hydrothermal treatment. The total pore area as measured by Hg-intrusion of a calcium phosphate ceramic of the present invention having needle-like surface topography may be as high as 1.8, 1.9, 2, 2.5, 2.7, 3.0, 3.5, 3.8 or even 4.0 $m^2/g$, or higher.

The osteoinductive calcium phosphate ceramic of the present invention typically has a specific surface area (BET) that is 0.5, 1, 1.5 or even 2 times higher than that of the corresponding calcium phosphate ceramic starting material prior to the hydrothermal treatment. The Specific Surface Area as measured by BET of a calcium phosphate ceramic of the present invention having needle-like surface topography may be as high as 1.25, 1.4, 1.5, 2, 2.4, or even 2.5 $m^2/g$, or higher.

An advantage of the osteoinductive material of the present invention in the form of (micro)particles or granules is that it has excellent flowing properties. The sand-like constitution of the (micro)particulate material allows it to be injected without an additional fluidic carrier. Thus, the material in such an embodiment may be used as an injectable, although it may also be used in admixture with for instance a fluidic carrier. Alternatively, the (micro)particles or granules may combined into composite material to form solid or semisolid blocks, as can suitably be used for instance for implantation.

In still another preferred embodiment of the material of the invention, the density of apatite needles is lower than 0.45/$µm^2$.

In another aspect, the present invention relates to the osteoinductive calcium phosphate of the invention for use as a medical implant material or tissue scaffold.

An osteoinductive calcium phosphate of the invention may suitably be used for inducing the formation of bone tissue in a living organism, as an implant material alone or combined with growth factors or/and cells for the production of autologous bone in a non-osseous site or for the production of a medical implant or device alone or combined with growth factors or/and cells.

An osteoinductive calcium phosphate of the invention may suitably be used in bone reconstruction such as for instance in maxillofacial surgery, or orthopaedic surgery.

In another aspect, the present invention relates to an osteoinductive calcium phosphate coating comprising an outer layer comprising apatite needles and, optionally, an inner layer that is in contact with the outer layer. In a preferred embodiment of this aspect, the osteoinductive calcium phosphate coating consists of a layer comprising apatite needles, wherein the layer forms a coating layer on a core material. The core material's surface may not be coated completely, but is preferably covered for at least 40-90% with the osteoinductive calcium phosphate coating. The core material may be any implantable material, for instance a bone supporting or bone reconstruction material, such as a metal (gold, steel wire, platinum, titanium), plastic (polyethylene, polytetrafluorethylene) or ceramic (ceramic oxide, carbon, calcium-phosphate ceramic, vitreous ceramic) material, preferably a calcium phosphate, more preferably BCP, or combinations of those materials.

In a preferred embodiment of the coating of the invention, the apatite is a hydroxyapatite.

In another preferred embodiment of the coating of the invention, the apatite needles have an average diameter of between 10-1500 nm.

In still another preferred embodiment of the coating of the invention, the density of apatite needles of the outer layer is lower than 0.45 needles/$\mu m^2$.

In yet another preferred embodiment of the coating of the invention, the thickness of the outer layer is between 1 and 1000 μm.

In still another preferred embodiment of the coating of the invention, the inner layer comprises a BCP.

In yet another preferred embodiment of the coating of the invention, the BCP comprises 4-20 wt. % apatite.

In still another preferred embodiment of the coating of the invention, the BCP is a sintered BCP.

In another preferred embodiment of the coating of the invention, the coating has a BET specific surface area above 0.9 $m^2/g$.

In still another preferred embodiment of the coating of the invention, the outer layer is a precipitate of apatites from the BCP of the inner layer following the hydrothermal treatment thereof at a temperature equal to or higher than 125° C.

In another aspect, the present invention provides an implantable object comprising the coating according to any one of the preceding embodiments of the coating of the invention.

DETAILED DESCRIPTION OF THE INVENTION

The terms "particle" and "granule" are used interchangeably herein, and are used herein to indicate a granular or powdery form of the calcium phosphate material. The particles may have an average size in a range of from 0.1 to 5 mm. A microparticle is a particle having a size less than 1 mm (i.e. several to several hundred micrometers).

The term "crystal" is used to indicate the individually recognizable and interconnected calcium phosphate elements as visible in SEM micrographs and which elements form the continuous matrix of the calcium phosphate. The term "crystal" in general refers to the basic spatial structure of the calcium phosphate molecules after the crystallization process, such as precipitation. The term "crystal" covers both grains and needles as defined herein.

Figure 1:
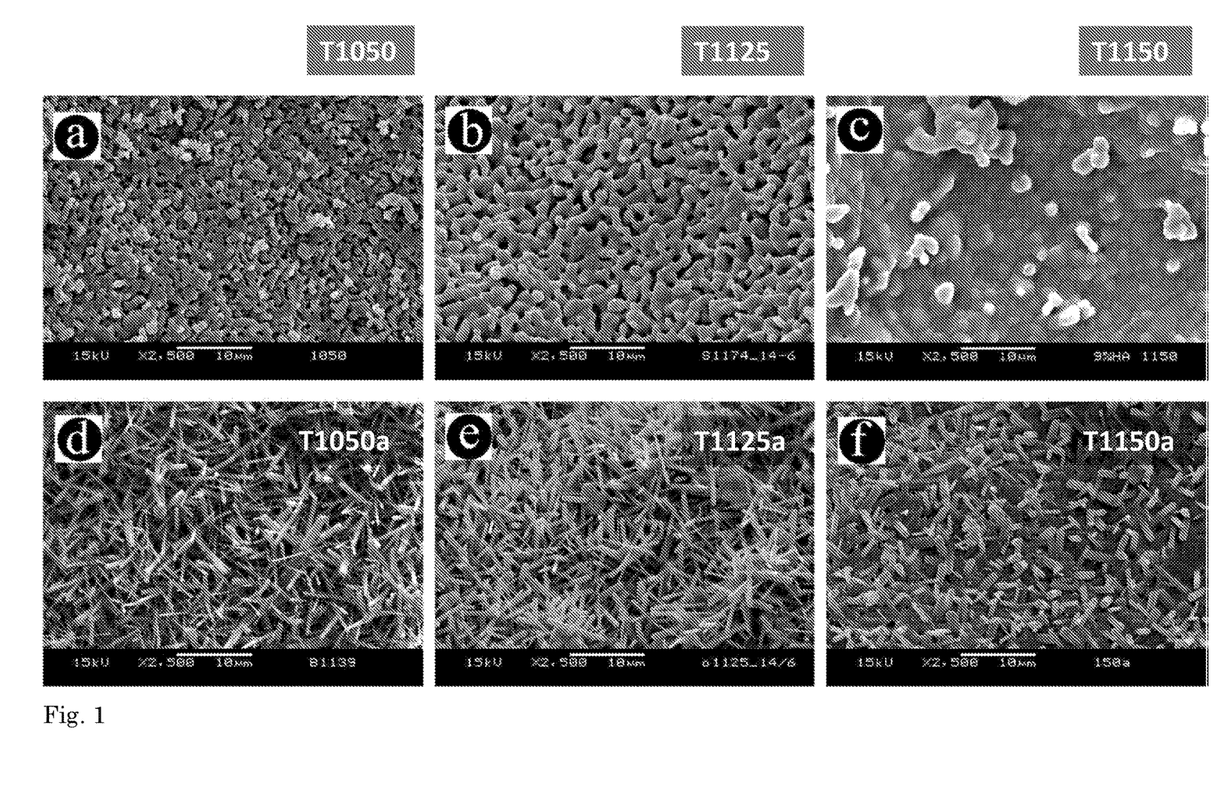
FIG. 1 shows SEM images of (a) T1050, (b) T1125, (c) T1150, (d) T1050a, (e) T1125a, and (f) T1150a. Pictures (d)-(f) are ceramics treated with 'hot/long' settings. No images are reported here for ceramics treated with 'cold/short' treatment as no changes in surface topography occurred.

The terms "grain" and "grain-like" are used to indicate that the calcium phosphate crystals have a globular nature or morphology thereby defining the surface topography of the calcium phosphate material. FIGS. 1a-c provide examples of grain-like surface topographies of the calcium phosphate, i.e. wherein the crystals are essentially consisting of grains. Grains generally have an average size in range of 0.1-5.0 μm.

The terms "needle" and "needle-like" are used to indicate that the calcium phosphate crystals have a spinal nature or morphology thereby defining the surface topography of the calcium phosphate material. FIGS. 1d-f provide examples of a needle-like surface topography of the calcium phosphate, i.e. wherein the crystals are essentially consisting of needles. Petal- or leaf-like structures are not included in the term needle-like, which term preferably is limited to a cylindrical or polygonal prism structure having a length of more than 1.5, 3, 4, 5, 6, 10, 20, 50 or 100 times its diameter (10-1500 nm).

The term "particles having irregular shapes" means that the particles of a calcium phosphate powder (which may itself also have a grainy structure) are not spherical.

The term "BCP", as used herein, refers to a composite of β-TCP and apatite, preferably hydroxyapatite (Ca/P ratio 1.5-1.67). In other words, the term "BCP" refers to a composite of β-TCP and apatite, preferably hydroxyapatite, comprising 1-99 wt. % apatite, preferably hydroxyapatite, and correspondingly 99-1 wt. % β-TCP, based on the weight of the calcium phosphate. Thus, the term "BCP", as used herein, includes all possible combinations of apatite, preferably hydroxyapatite, and β-TCP within the range of wt. % as indicated above.

The term "apatite", as used herein, refers to any of a group of calcium phosphate minerals that is denoted by the repeating stoichiometric chemical formula $Ca_5(PO4)_3(OH)$, and any other non-stoichiometric and/or deficient apatite due to partial substitutions of the OH group by e.g. $F^-$, $Cl^-$, $CO_3^{2-}$, HCO$_3^-$, or any other anion and/or the partial substitution of the PO$_4$ group by e.g. HPO$_4^{2-}$, CO$_3^{2-}$, HCO$_3^-$, or any other anion and/or the partial substation of Ca$^{2+}$ by e.g. Mg$^{2+}$, Sr$^{2+}$, Ba$^{2+}$, Na$^+$, or any other cation (Elliot, J. C., 1994. Structure and Chemistry of the Apatites and other Calcium Orthophosphates, Amsterdam: Elsevier). These partial substitutions lead to variation in the Ca/P ratio.

The term "specific surface area" indicates the surface area of the CaP particles as determined BET analysis. With the Brunauer, Emmett and Teller (BET) method (J. Am. Chem. Soc., 1938, 60, 309), the surface area of a powder is estimated from the amount of gas adsorbed in relationship with its pressure, at the boiling temperature of liquid gas under normal atmospheric pressure and expressed in m$^2$/gram.

The term "total pore area" indicates the accessible volume of liquids (e.g. biological fluids, cells) that can flow through the implant (i.e. through CaP particles). This total available pore area is determined by mercury intrusion, using the cylindrical pore model (are disclosed in "An Introduction to the Physical Characterization of Materials by Mercury Intrusion Porosimetry with Emphasis on Reduction and Presentation of Experimental Data," Paul A. Webb, pp 1-22, Micromeritics Instrument Corporation, Norcross, GA, January 2001) and expressed in m$^2$/gram.

The term "protein adsorption" indicates the amount of protein absorbed by a volume of 1 cc of the calcium phosphate when soaked in 2 ml of an aqueous solution containing 1% foetal bovine serum (FBS) and 25 ppm NaN$_3$, or 400 µg/ml bovine serum albumin (BSA) and 25 ppm NaN$_3$, after incubation at 37° C. for 24 hrs, whereby the amount absorbed is 100% minus the percentage remaining in solution and of which the protein content is determined before and after contact with the calcium phosphate, using for instance a BCA™ Protein Assay Kit (Pierce Biotechnology Inc., Rockford, Ill., USA).

The term "sintering" and "sintered" refer to a process of thermal treatment of the CaP essentially at temperatures in excess of 1000° C., such as between 1000° C. and 1300° C., preferably between 1050° C. and 1275° C. The sintering process results in densification of the calcium phosphate material. Depending on the increase in the density required, the sintering process can be performed for a duration of 1-10 hrs.

The term "outer layer", as used herein, refers to a layer of an osteoinductive coating that comprises apatite needles, wherein the apatite needles are attached to or deposited on a core material base an a deposition or attachment surface, and wherein optionally between the core material base and the outer layer, an inner layer is positioned, and wherein the part of the outer layer opposite from the core material base forms the surface of the coating that is exposed to the tissue when implanted in a human or animal body. It is an embodiment of this invention that the outer layer is the only layer present on the core material base, and, hence, that it is the only material of an osteoinductive coating of the invention. It is also envisaged herein that an osteoinductive coating comprises an inner layer that is in contact with the outer layer.

The term "inner layer", as used herein, refers to a layer of an osteoinductive coating that comprises, or, preferably, consists of, BCP and wherein the inner layer is in contact with an outer layer. The inner layer is located more towards the core of the ceramic as compared to the outer layer. In some minor instances, the inner layer may be exposed to the environment as a result of granule fragmentation or as a result of physical hindrance during hydrothermal treatment (e.g. some parts of the granules in contact with the glass dish will not lead to apatite needle formation).

The Pre-Treatment Calcium Phosphate Material

A starting material useful in aspects of the present invention and amenable for an increase in osteoinductive capacity by a method of this invention is characterized by being a sintered calcium phosphate having a surface topography consisting essentially of calcium phosphate grains. Thus, the structure of the calcium phosphate matrix itself is upon microscopic observation not smooth but grainy, wherein the structural material is structurally organised in the form of packed grains.

The starting material preferably comprises macropores. The starting material preferably has an essentially open, porous structure, wherein the individual pores are interconnected by openings or voids. The material or coating of the present invention is preferably porous, both prior and post-hydrothermal treatment. Washing (e.g. sonicating) the material prior to hydrothermal treatment is preferred. The starting sintered calcium phosphate material is preferably porous. The starting sintered porous calcium phosphate material may in embodiments comprise micropores, but in preferred embodiments does not comprise micropores (pores <5 µm).

The apatite is preferably a hydroxyapatite, fluoro-apatite, chloro-apatite, carbonated apatite or a calcium deficient apatite. The apatite may be a combination of at least two apatites selected from hydroxyapatite, fluoro-apatite, chloro-apatite, carbonated apatite calcium deficient apatite and non-stoichiometric apatite. More preferably, the apatite is essentially a hydroxyapatite. This means that the apatite consists of at least 50 wt. % hydroxyapatite, more preferably between 70-90 wt. % hydroxyapatite, and most preferably 91, 92, 93, 94, 95, 96, 97, 98, 99 or 100 wt. % hydroxyapatite, based on the weight of the apatite, for example as measured by X-ray diffraction.

The skilled person knows that an apatite may be imperfect, for example by being low, or even deficient, in calcium and hydroxide ions, but rich in substitutional impurities. In this context, when the term "hydroxyapatite" is used, it refers to an apatite that is essentially a hydroxyapatite, but allows for impurities. An example of such an impurity is the presence of one or more fluoro and/or chloro chemical groups in the hydroxyapatite. Thus, the term "hydroxyapatite", as used herein, includes an apatite that is essentially hydroxyapatite, but that also comprises one or more fluoro-apatites, chloro-apatites, carbonated apatites, non-stoichiometric and/or calcium-deficient apatites.

The starting materials as used herein are calcium phosphates comprising preferably at least 60 wt. %, more preferably at least 70 wt. %, and even more preferably at least 80 wt. % of β-TCP. The calcium phosphates starting material preferably comprises about 4-20 wt. % of apatite, preferably hydroxyapatite, based on the weight of the calcium phosphate. A BCP useful as a starting material may suitably be a BCP obtained by precipitation from an aqueous solution at low temperature or by a high temperature (thermal) process.

Methods for producing CaP starting materials may comprise the steps of providing an aqueous slurry of a calcium phosphate powder, a foaming agent and optionally a porogenic agent in water; subjecting the slurry to conditions which cause foaming of said slurry; drying the resultant foamed slurry and optionally removing the porogenic agent, and sintering the dried and foamed slurry to obtain an optionally porous sintered calcium phosphate ceramic. The method may optionally be followed by the steps of milling the sintered calcium phosphate ceramic to particles and collecting the particles having a desirable particle size.

The CaP starting materials for use in methods of this invention are sintered materials, meaning that they have preferably been subjected to temperatures in excess of 1000° C.

Suitable CaP starting materials may for instance be produced by aging aqueous mixtures of calcium nitrate tetrahydrate and di ammonium hydrogen phosphate at elevated pH, followed by powdering the resulting deposit, creating porosity in the presence of a pore-forming agent such as hydrogen peroxide, and sintering the resulting green bodies. Such methods are for instance described in U.S. Pat. No. 6,511,510. Preferably, the calcium phosphates of the present invention are formed by a process involving sintering of an unsintered calcium phosphate (green body) at a temperature between 800° C. and 1300° C., preferably between 1000° C. and 1275° C., more preferably between about 1050° C. and 1200° C., optionally under pressure. Preferably, the sintering is carried out at a temperature between 1075° C. and 1175° C., 1100° C. and 1150° C. The duration of the sintering step may suitably be chosen and optimized to result in the best needle-like structure topography following the hydrothermal treatment, preferably between for instance 4 and 10 hours, preferably between 6 and 9 hours.

The properties of the CaP starting product can be adjusted by selecting specific combinations of temperature, pressure and calcium phosphate starting materials. For example, pure HA is formed by using an apatite with a Ca/P ratio of 1.67, whereas TCP is formed by using an apatite with a Ca/P ratio of 1.5. The present invention, however, relates to Ca/P ratios varying between 1.51 and 1.66 (border values included), that result in a combined apatite-TCP, preferably hydroxyapatite-TCP, ceramic referred to as BCP and may for instance be sintered to provide the sintered CaP ceramic with different amounts of apatite, preferably hydroxyapatite, and TCP.

The sintering parameters may be chosen to adjust the macroporosity of the starting material. The macroporosity of the ceramics may in some embodiments of a method for their production be due to gaps left between the sintered particles, which—in turn—is influenced by the crystallization of the CaP or the porogenic agent used. The sintering parameters may also be chosen to adjust the grain size of the starting material. The grain size of the ceramics may in some embodiments of a method for their production be due to phase transformation of the green body due to sintering, which—in turn—is influenced by the sintering time and sintering temperature.

In accordance with a preferred embodiment of the invention, the CaP starting material is made up of interconnected crystals or grains. The size of the grains is in a preferred embodiment preferably between 50 and 3000 nm or 0.05 and 3 µm, more preferably between 0.1 and 2 µm, still more preferably between 0.1 and 1.5 µm, and even more preferably between 0.5 and 2.5 µm. The starting material is preferably BCP. The BCP starting material is preferably in the form of a powder having a granule or particle size in the range of 50 to about 5500 µm, preferably 500-1500 µm, or 1000-4000 µm.

The Hydrothermal Treatment Process

In short, a method for producing a sintered calcium phosphate ceramic with improved osteoinductive performance and based on needle-like surface topography may be performed as follows:

In a highly preferred embodiment of a sintered calcium phosphate, the first step is to provide a sintered calcium phosphate ceramic as a starting material. In such a preferred embodiment, an aqueous slurry of a calcium phosphate powder, a foaming agent, and a porogenic agent may be provided in a solvent. The slurry may then be subjected to conditions which cause foaming of said slurry. Subsequently, the resultant foamed slurry may be pre-dried and the porogenic agent may be removed by pre-sintering. Then, the pre-dried and foamed green bodies may be sintered to obtain a sintered calcium phosphate ceramic, optionally after the green bodies have been milled or crushed into smaller particles. Finally the sintered calcium phosphate ceramic starting material (which may optionally be milled or crushed into smaller particles) may then be subjected to hydrothermal treatment to cause development of CaP needles on the surface of the ceramic thereby obtaining a sintered calcium phosphate ceramic with needle-like surface. As indicated, if unmilled green bodies are subjected to sintering and hydrothermal treatment, the method may be followed by the steps of milling said calcium phosphate ceramic to granules and collecting the granules, optionally in various granule size fractions. It will be understood that since the hydrothermal treatment is essentially a surface treatment of the sintered calcium phosphate, it is preferred that if particles with improved osteoinductivity are to be obtained, particles of a desired particle size are provided prior to the hydrothermal treatment step in order to modify the surface of said particles, to thereby provide the particles of the invention.

As said, the preparation of a green body may suitably comprise the formation of a slurry of a calcium phosphate (CaP), wherein said CaP is preferably in the form of a powder, suspended in a solution containing a foaming agent. The concentration of the foaming agent (e.g. $H_2O_2$) in the foaming agent solution is suitably in the range from 0.1% to 10.0% and the solvent is suitably water. The ratio wherein foaming agent solution (e.g. $H_2O_2$, 0.1-10.0% in water) and calcium phosphate are mixed to form the slurry is suitably between 1 and 300 mL of foaming agent solution per 100 g of CaP. The amount of porogenic agent (e.g. naphthalene or wax granules, <2000 µm) used per 100 g of CaP is suitably between 0-150 g. The porogenic agent may be suspended in a solvent. The ratio wherein said solvent and calcium phosphate are mixed is suitably between 0 and 100 mL of solvent per 100 g of CaP, or the content ratio of said solvent in water is suitably between 0 and 50% by volume. The slurry may be then foamed and dried at for instance 50-120° C. and then pre-sintered at for instance 800-1100° C. for 1-6 hours to form the green bodies, which are then sintered at for instance 1000-1300° C. for 3-12 hours. The composition of this ceramic is: HA 4-18% and beta-TCP: 96-82%. The sintered calcium phosphate ceramics are then hydrothermally treated in water at 135° C., 99 min and 2-4 bars, dried at 40-100° C. and milled to form granules with may be collected (and provided) in different sizes.

The CaP starting material as defined above is subjected to hydrothermal treatment resulting in modification of the CaP surface topography.

The method comprises subjecting the calcium phosphate material to a hydrothermal treatment at a temperature higher than or equal to 125° C., preferably between 125-300° C., more preferably between 125-200° C., and most preferably between 125-150° C. for a duration sufficient to change calcium phosphate grains on the surface of the material into calcium phosphate needles. Particularly preferred is a temperature of the hydrothermal treatment that is between 130-140° C. even more preferably around 135(+/−2)° C.

The hydrothermal treatment involves placing the calcium phosphate starting material in contact with water, preferably by submersion into water, and subjecting the calcium phosphate ceramic starting material to a temperature of between 125-150° C., preferably between 130-140° C., more preferably around 135(+/−2)° C., for a duration of at least 30 min at preferably about 2-4 bars or for equivalent durations at other pressures, while the calcium phosphate remains in contact with water. Preferably, soaking in unheated water does not constitute hydrothermal treatment as defined herein. Also, contacting the calcium phosphate to steam does preferably not constitute hydrothermal treatment as defined herein. Hydrothermal treatment preferably encompasses autoclaving the calcium phosphate while in contact with water, preferably submerged in water. Preferably, the duration of the hydrothermal treatment is at least 40, 50, 60, 75, 100, 200, 300, or 400 min or longer at 2-4 bars, or for equivalent durations at other pressures. More preferably, the treatment comprises subjecting the material to the indicated temperature for a duration of about 100 min at 2-4 bars.

Following the above hydrothermal treatment, the grainy surface feature of the starting CaP material has changed into a needle-like surface feature consisting of tethered nano-needles covering the entire surface of the granules. The diameter of these nano-needles may vary in range between 10-1500 nm With the smaller dimensions of about 10 and 600 nm deriving from the smaller grain-size CaPs, whereas the larger needle size range of between about 400 to 1500 nm is from the larger grain-size CaPs. Preferably, the needle size diameter is lower than 800 nm, more preferably it is between 100 and 750 nm and most preferably it is between 200 and 700 nm. Average needle diameter of 600-680 nm may regularly be observed in the instance of a material indicated herein as T1125a.

Figure 2:
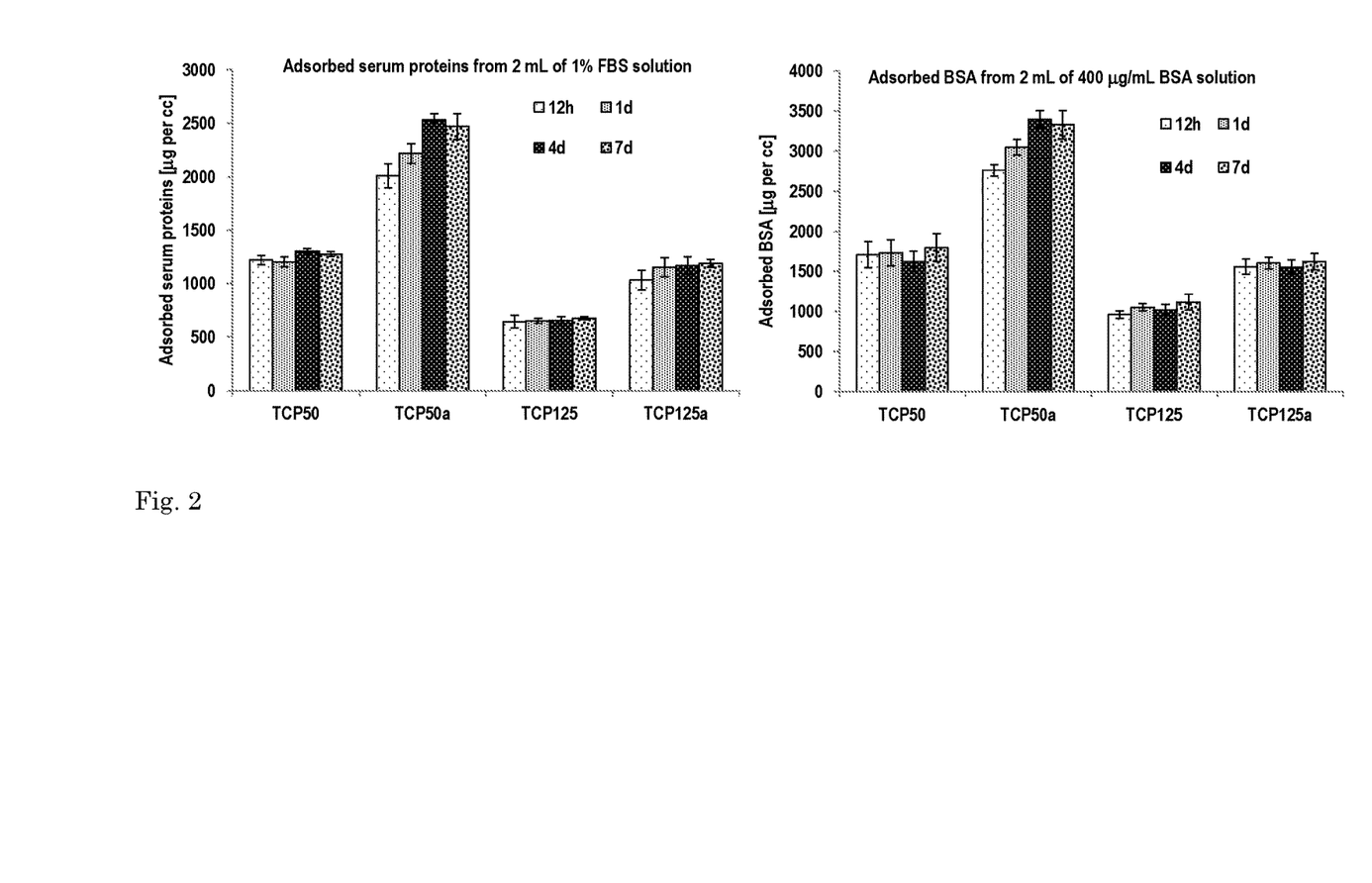
FIG. 2 (left) shows serum protein adsorption (in μg per cc) and (right) albumin protein adsorption (in μg per cc).

From FIG. 2 and Table 3 it follows that the grain size depends on the sintering temperature. Also, FIG. 2 and Table 3 show that when the needle size diameter is higher when the sintering temperature is higher, if the parameters of the hydrothermal treatment are constant. It was found that, when adjusting the settings of the hydrothermal treatment, it is possible to obtain a needle size diameter in the order of magnitude of a T1125a ceramic (see Table 3) when hydrothermally treating a T1150 ceramic (see Table 3) for a longer duration at a higher temperature. In other words, the grain size of the sintered starting material is not in itself determinative for the question whether an osteoinductive material or coating of the invention is obtained after a hydrothermal treatment. It is envisaged here that the starting materials of the materials and coatings of the invention are sintered at a temperature higher than 1125° C. and afterwards are subjected to a hydrothermal treatment for a duration and temperature sufficient to obtain a material or coating of the invention having a preferred needle size diameter as indicated in the previous paragraph.

In preferred embodiments of this invention the starting material is fully submerged in aqueous solution (preferably water) during the hydrothermal treatment. Alternatively, the method may be performed under relative humidity levels of about 100%.

Preferably the hydrothermal treatment comprises subjecting the calcium phosphate ceramic material to a temperature of between 130-140° C., more preferably around 135(+/−2)° C.

Preferably the hydrothermal treatment comprises subjecting the calcium phosphate ceramic material to the elevated temperature for a duration of at least 10 min, preferable for a duration of at least 40, 50, 60, 75, 100, 200, 300, or 400 min or longer. The duration of the hydrothermal treatment is essentially sufficient to change calcium phosphate grains on the surface of the material into calcium phosphate needles. This change may be determined by SEM.

Preferably the hydrothermal treatment comprises subjecting the calcium phosphate ceramic material to the elevated temperature while submerged in water.

Preferably the hydrothermal treatment comprises subjecting the calcium phosphate ceramic material to the elevated temperature for the indicated duration, while the material is preferably at 2-4 bars. Other pressures may be used, but durations may be adapted to optimize surface modification of the calcium phosphate ceramic. Preferably, for the duration of the hydrothermal treatment the material occurs at 2-4 bars. In a most preferred embodiment, the hydrothermal treatment comprises subjecting the material to the indicated temperature for a duration of about 100 min at 2-4 bars.

The method of this invention is directed to changing the surface topography and thereby the osteoinductive capacity of a calcium phosphate surface. In preferred embodiments, the term "surface" as referred to herein refers to the top 0-1.0 mm measured from the outside of the CaP material.

The Calcium Phosphate Material with Improved Osteoinductivity

Following the above hydrothermal treatment, the grainy surface feature of the starting material has changed into a needle-like surface feature consisting of tethered nano-needles covering the surface of the granules. The diameter of these nano-needles may vary in range between 10-1500 nm. With the smaller dimensions of about 50 and 400 nm deriving from the smaller grain-size CaPs, whereas the larger needle size range of between about 350 to 1100 nm is from the larger grain-size CaPs.

In a calcium phosphate material obtained by a method of the present invention, the surface of the material has changed significantly, whereas the underlying (deeper) material may be essentially unchanged. Hence, in an improved calcium phosphate ceramic subject of this invention 80% of the grains within the material may be unchanged, whereas this primarily accounts to sub-surface (>deeper than 1.0 mm-1 cm from the surface) grains.

The improved calcium phosphate ceramics of the invention preferably have a surface topography of needle-like crystals with diameters in a range of 0.01-1.50 µm, more preferably 50-1250 nanometers.

The calcium phosphate materials and coatings of the present invention preferably have a needle density lower than $0.45/\mu m^2$, more preferably between $0.10/\mu m^2$ and $0.40/\mu m^2$, even more preferably between $0.25/\mu m^2$ and $0.39/\mu m^2$, oand still more preferably $0.28/\mu m^2$, $0.29/\mu m^2$, $0.30/\mu m^2$, $0.31/\mu m^2$, $0.32/\mu m^2$, $0.33/\mu m^2$, $0.34/\mu m^2$, $0.35/\mu m^2$, $0.36/\mu m^2$, $0.37/\mu m^2$ or $0.38/\mu m^2$.

The specific surface area and total pore area of the material of the invention are markedly higher than that of the sintered calcium phosphate prior to the hydrothermal treatment. In general an increase in specific surface area and total pore area due to the needle formation is noticed that exceeds an increase in 50, 80, or even 100%, i.e. a doubling of the initial specific surface area and total pore area is noticeable when analysed by BET analysis or by mercury intrusion, respectively.

The total pore area of the material of the present invention is typically above 1.8 $m^2/g$ when measured by Hg intrusion.

The specific surface area of the material of the present invention is typically above 1.25 or even 1.4 $m^2/g$ when measured by BET.

The preferred needle diameter of the crystals, size of macropores, specific surface area and total pore area result in high concentration of protein adsorption onto the ceramics and high bone forming ability (inductive bone formation in non-osseous sites).

The improved sintered calcium phosphate of the invention preferably exhibits a surface protein adsorption of more than 40%, more preferably more than 60%, still more preferably more than 75% (40-80%) determined as described herein above in 24 hrs. In particular, the improved sintered calcium phosphate of the invention preferably exhibits a surface protein adsorption wherein more than 250 µg, preferably more than 300 preferably more than 500 µg, preferably more than 1000 µg, preferably more than 1500 µg or higher of BSA is adsorbed to the surface of 1 ml of calcium phosphate material from 2 ml of a BSA solution at 400 µg BSA/ml.

In aspects of this invention, the calcium phosphate with improved osteoinductive capacity may take the form of a calcium phosphate coating, i.e. an osteoinductive calcium phosphate coating. Such a coating may be obtained by a method as described herein and comprises an outer layer and may comprise an inner layer. The coating may have a thickness of several micrometers to several millimeters or even centimeters. Preferably, the thickness of the outer layer of the coating is between 1 and 1000 µm, preferably between 1 and 500 µm, more preferably between 1 and 200 µm and most preferably between 1 and 100 µm. The thickness of the outer layer is measured by means known to the skilled person and involves measuring the outer layer after providing a cross section of a material of the invention. The thickness of the layer comprising apatite needles in a material of the invention is correspondingly preferably between 1 and 1000 µm, preferably between 1 and 500 µm, more preferably between 1 and 200 µm and most preferably between 1 and 100 µm. The calcium phosphate coating may be used as an improved surface on other (e.g. non-osteoinductive) materials that require improvement of their osteoinductive capacity, including, but not limited to, other calcium phosphates, metals, ceramics, glass, polymers or composite materials. The improved osteoinductive coating can be produced by coating the surface of a material of which the osteoinductivity is to be improved with a calcium phosphate starting material as described herein, and subjecting the coated material to a method for improving osteoinductive capacity as described herein. The resulting coated product has improved osteoinductive properties. Alternatively, the improved osteoinductive calcium phosphates having the improved needle-like surface topography subject of this invention may suitably be attached or bonded to the surface of a material of which the osteoinductivity is to be improved, i.e. a core-material base, for instance by gluing, molding or pressing. It is envisaged herein that the outer layer of the coating of the invention may suitably be a precipitate of the inner layer of the coating of the invention following the hydrothermal treatment of said inner layer by using a method of the present invention. Alternatively, the improved osteoinductive calcium phosphates having the improved needle-like surface topography subject of this invention may suitably be provided in the form of an injectable, either alone in the form of a "powder" or in combination with a liquid carrier in the form of a paste, or a cement and may then be applied to the surface of a material of which the osteoinductivity is to be improved.

An improved calcium phosphate ceramic of the invention is preferably prepared by a process using oven dried milled calcium phosphate powders having irregular shapes. Such materials are preferred over the use of spray dried calcium phosphate powders having regular spherical particles. In addition, sintering temperatures are preferably between 800 and 1200° C. For individual calcium phosphates, sintering temperatures may be further optimized.

The material of the present invention may for instance be used for inducing the formation of bone tissue in a living organism.

The material of the present invention may suitably be used as an implant material, i.e. as a scaffold, for the production of autologous bone in a non-osseous site. This ability is due to the highly osteoinductive properties of the material.

The material of the invention may thus be used as a medical implant or medical device formed of a calcium phosphate. It is also possible that the material is used in combination with a medical implant of a different material, such as a metal or a polymeric material, on which the osteoinductive material according to the invention is present in the form of a coating.

It should be noted that the various uses of the material of the present invention include general musculoskeletal surgical applications in bone repair, as well as applications in dental or orthopedic surgery.

The invention will now be illustrated by way of the following non-limiting examples. These Examples describe methods to improve bone forming ability of calcium phosphate ceramics (i.e. sintered calcium phosphates), wherein the calcium phosphate is a BCP.

EXAMPLES

Example 1 Influence of Autoclave Settings on Needle Formation 1.1. Preparation of Biphasic Calcium Phosphate Ceramics Biphasic calcium phosphate (BCP) powder (92-96% β-TCP and 8-4% HA) was prepared by mixing Ca(OH)$_2$ and H$_3$PO$_4$ in an aqueous solution to allow CaP precipitation. The Ca/P ratio was adjusted to obtain final CaP ceramics with different TCP and HA content. The following Ca/P rations were produced: 1.500 (for ~100% TCP), 1.509 (for ~5% HA/95% TCP), 1.518 (~10% HA/90% TCP., 1,534 (~20% HA/80% TCP), 1,568 (~40% HA/60% TCP), or 1.636 (~80% HA/20% TCP) The CaP precipitate was filtered and dried into CaP powder. This CaP powder was used to prepare a slurry in demineralized water containing H$_2$O$_2$ (1-2%), 0-500 µm wax particles (40-60-g/100 g powder) and ethanol (8-10%). Thereafter, the slurry was foamed at 40-80° C. and pre-sintered at 1000° C. When wax was fully burnt out, the porous cake was crushed into particles (0-5 mm) and sintered at different temperatures, i.e. 1050° C., 1125° C. and 1150° C., to obtain a porous calcium phosphate ceramics with different surface topography but same chemical composition.

1.2. Characterization of Biphasic Calcium Phosphate Ceramics

The ceramics were characterized regarding their HA/TCP content ratio using X-ray diffractometer (XRD, Table 1). The results show that the ceramics are biphasic calcium phosphates with comparable HA/TCP content ratio independently from the sintering temperature. Scanning electron microscopy (SEM) images demonstrate that the sintering temperature has effect on the surface structure, i.e. the higher the sintering temperature and the bigger the grain size with decrease in porosity (FIG. 1a-c).

1.3. Hydrothermal Treatment of the Ceramics

Granules were laid down in a glass dish. The layer was submerged in demineralized water, whereby the level of the water was at least 2 cm above the surface of the layer of granules. The dish containing granules was placed in an autoclave (Astell, AVX 040). Two different settings were applied to as indicated in Table 2. When the treatment was finished, the materials were taken out to cool down and dry at 80±10° C.

1.4. Characterization of the Hydrothermally Treated Ceramics

Scanning electron microscopy in the secondary electron mode (SEM; JEOL) was used to evaluate the surface topography of the starting granules, and the sizes of ~500 crystals for each material was measured. The grain size of the starting material was measured and median values were calculated. After hydrothermal treatment, the diameter of the newly formed needles was measured, and median values were calculated. All measurements were performed with the tool 'length measurement' in ImageJ (v1.43u, NIH, USA) using the SEM scale bar as reference. In this phase the specifications of the starting materials and the hydrothermal treatment settings for a successful surface modification have been established.

The SEM images demonstrated that only the hydrothermal treatment with settings 'hot/long' causes the disappearance of the typical grain ceramic surface structure and leads to the growth of needle-like structures (FIG. 1d-f), while 'cold/short' settings did not lead to needle formation in any of the considered ceramics. Measurements revealed that such needle-like components have increasing diameter with the increase in the grain size of the starting ceramic (Table 3).

The specific surface area (SSA) of the samples was determined by the change in concentration of $N_2$/He (30/70) gas as adsorption and desorption proceed using the Monosorb™ analyser (Quantachrom Instruments, USA), for determinations of single-point B.E.T. surface area. A weight of 1.0000±0.0001 gram of dry sample is placed in a 4.8 cm$^3$ cell volume. $N_2$/He (30/70) gas is applied with a pressure of 140 kPa, and desorbed for ~30 min. This operation is repeated 3-folds.

The total pore area of the sample was determined by mercury intrusion using Micromeritics mercury porosimeter (AutoPore). A weight of 0.4-0.7 gram of sample was placed in a 3 cm$^3$ bulb volume penetrometer with stem volume of around 1.1-1.2 ml to achieve approximately 50-90% stem volume use. The filled penetrometer was inserted into the instrument for mercury intrusion (Hg contact angle 130.000 degrees, Hg density 13.5310 g/mL). The evacuation was realized using a 50 μm Hg for 5 minutes, followed by mercury filling at 0.22 psia equilibrated for 10 seconds.

BET and mercury intrusion measurements revealed that the needle formation in any of the considered ceramics lead to an increase of specific surface area and total pore area respectively (Table 3).

Protein adsorption on granules was performed on two solutions:
aqueous solution containing 1% vol. foetal bovine serum (FBS) and 25 ppm $NaN_3$.
aqueous solution containing 400 μg/mL bovine serum albumin (BSA) and 25 ppm $NaN_3$.

Needle density on granules was determined by counting the number of needles visible on ×5000 SEM images (window size 424,6528 μm$^2$). The density was calculated per μm$^2$.

Sterile granules (0.2 cc) of the ceramics were placed in 2 mL of the protein solutions (in quintuple). They were incubated at 37±0.5° C. and 5% $CO_2$ for one week. Proteins adsorbed (i.e. serum proteins and albumin) were measured after 12 hours, 1 day, 4 days and 7 days using micro BCA assay kit and spectrophotometer with absorbance filter of 595 nm. The protein adsorbed by the samples (expressed in μg per cc for FBS, and in μg per cc for BSA) was estimated through internal calibration protein curves for FBS and BSA. Analyses have been done on materials before and after the treatment.

FIG. 2 shows that, independently from the type of the starting material (i.e. TCP1050 or TCP1125), the hydrothermal treatment significantly increased the potential to adsorb proteins thanks to the increase in surface area.

1.5. Conclusion

Hydrothermal treatment (e.g. 135° C., 99 min, 2-4 bar) of BCP ceramics tested herein generated needle-like surfaces on such ceramics regardless of the sintering temperature, where the needle diameter increases with the grain size of the treated ceramic. The formation of needles led to an increase of specific surface area, total pore area and subsequently total protein adsorption.

TABLE 1

HA/TCP content ratio of the ceramics prepared in Example 1.

|  | T1050 | T1125 | T1150 |
|---|---|---|---|
| HA [%] | 8 | 6 | 9 |
| TCP [%] | 92 | 94 | 93 |

TABLE 2

Hydrothermal treatment settings (Astell autoclave, AVX 040).

| Setting | 'cold/short' | 'hot/long' |
|---|---|---|
| T [° C.] | 121 | 135 |
| Time [min] | 30 | 99 |
| Pressure [bar] | 2-4 | 2-4 |

TABLE 3

Surface characterization of materials prior and after hydrothermal treatment[1].

|  | T1050 | T1125 | T1150 | T1050a | T1125a | T1150a |
|---|---|---|---|---|---|---|
| Average grain size | 0.73 ± 0.21 | 1.85 ± 0.45 | 2.29 ± 0.69 | n/a | n/a | n/a |
| Median range | 0.60-0.67 | 1.53-1.60 | 2.20-2.27 |  |  |  |
| Average needle diameter [nm] | n/a | n/a | n/a | 341 ± 171 | 579 ± 198 | 801 ± 201 |
| Median diameter range [nm] |  |  |  | 300-312 | 540-562 | 828-840 |

TABLE 3-continued

Surface characterization of materials prior and after hydrothermal treatment[1].

| | T1050 | T1125 | T1150 | T1050a | T1125a | T1150a |
|---|---|---|---|---|---|---|
| Needle density/$\mu m^2$ | n/a | n/a | n/a | 0.36 ± 0.08 | 0.32 | 0.46 ± 0.07 |
| Min-max values/$\mu m^2$ | | | | 0.26-0.51 | | 0.39-0.62 |
| Specific Surface Area by BET [$m^2/g$] | 1.2 | 0.6 0.5 | 0.6 0.5 | 2.5 | 1.0 1.4 | 0.9 0.7 |
| Total pore area by Hg intrusion [$m^2/g$] | 1.8 1.5 | 1.3 | NM[2] | 4.4 | 2.7 | NM[2] |

[1]two values indicate two separate measurements;
[2]NM: not measured

Example 2 Influence of HA/TCP Ratio on Crystal Formation 2.1. Preparation of Biphasic Calcium Phosphate Ceramics BCP powders, with various HA/TCP content ratio were used to prepare ceramics following the procedure described in § 1.1 as described above XRD of the final ceramics shows that their HA/TCP content ratio did not change as compared to the starting powder used for their preparation.

2.2. Hydrothermal Treatment

All ceramic have been then hydrothermally treated according to the protocol described in § 1.3, with settings 'hot/long'.

2.3. Characterization of the Hydrothermally Treated Ceramics

SEM analysis showed that the HA/TCP content ratio of the starting calcium phosphate ceramic plays a key role in determining the growth of the needles (Table 4). The needle dimension and shape were comparable to those observed in Example 1. A narrow range of HA content is thus required for the successful needle formation. The general conclusion that needle-formation only occurs only on the surface of BCP ceramics, is substantiated by the observation that no needle-formation occured on the surface of calcium phosphate ceramics with 100 wt. % β-TCP after hydrothermal treatment. It was also seen that needle formation did not occur on 100 wt. % HA ceramics after a hydrothermal treatment.

2.4. Conclusion

Taking the results from this Example and from Example 1, hydrothermal treatment of grain-structured biphasic calcium phosphate ceramics generates needle-like surfaces on such ceramics, when the HA content of the starting ceramics is between 5 and 20%.

TABLE 4

HA/TCP content ratio of the ceramics prepared in Example 2 and results after hydrothermal treatment.

| | HA [%] | | | | | |
|---|---|---|---|---|---|---|
| | 1 | 2 | 7 | 18 | 35 | 79 |
| | TCP [%] | | | | | |
| | 99 | 98 | 93 | 82 | 65 | 21 |
| Needle formation | no | no | yes | yes | no | no |

Example 3 Osteoinductive Potentials 3.1. Experimental Setup

One cc of granules (1-2 mm) of T1050, T1050a and T1125a (as prepared in Example 1) were implanted in the paraspinal muscles of eight skeletally mature mongrel dogs (male, 1-4 years old, weight 10-15 kg) for 12 weeks to evaluate the tissue reaction and osteoinductive property of the new CaP ceramics. A negative control TCP ceramic without needle was used to validate the results of these experiments (TCP negative control)).

3.2. Implantation Protocol

The surgical procedure was performed under general anaesthesia (pentobarbital sodium, Organon, the Netherlands; 30 mg kg$^{-1}$ body weight) and sterile conditions. The back of the dogs was shaved and the skin was cleaned with iodine. A longitudinal incision was made and the paraspinal muscle was exposed by blunt separation. Longitudinal muscle incisions were subsequently made with a scalpel and separate muscle pouches were created by blunt separation. The composites granules were then placed in the pouches and the wound was closed in layers using silk sutures. After surgery, the animals received an intramuscular injection of penicillin for three consecutive days to prevent infection. After 6 weeks, all animals received an injection of the fluorescent dye calcein (2 mg kg$^{-1}$ body weight) to study the time onset of bone formation by calcein labelling.

3.3. Harvest and Histological Processing

Twelve weeks after implantation, the animals were sacrificed and the samples were harvested with surrounding tissues and fixed in 4% buffered formaldehyde solution (pH=7.4) at 4° C. for one week. After rinsing with phosphate buffer saline (PBS, Invitrogen), the samples were trimmed from surrounding soft tissues, dehydrated in a series of ethanol solutions (70%, 80%, 90%, 95% and 100%×2) and embedded in methyl metacrylate (MMA, LTI Nederland, the Netherlands). Non-decalcified histological sections (10-20 mm thick) were made using a diamond saw microtome (Leica SP1600, Leica Microsystems, Germany). Sections were stained with 1% methylene blue (Sigma-Aldrich) and 0.3% basic fuchsin (Sigma-Aldrich) solutions.

3.4. Histological Analysis

The sections were observed with a light microscope (Nikon Eclipse E200, Japan) to analyze the tissue reaction and bone formation in detail. The stained sections were scanned using a slide scanner (Dimage Scan Elite 540011, Konica Minolta Photo Imaging Inc, Tokyo, Japan) to obtain overview images for histomorphometrical analysis. Histomorphometry was performed on the scanned images using Photoshop CS5 software (v12, Adobe Systems Benelux BV). Firstly the whole samples were selected as a region of interest and the number of pixels was read as ROI. Then both the material and the mineralized bone were pseudo-coloured and their pixels were read as M and B respectively. The percentage of bone in the available space of the explants ($B_p$) was determined as $$B_P = 100 \times B/(ROI - M)$$

Unstained histological sections were observed at fluorescent microscopy (Nikon Eclipse E600, Japan; camera Nikon FDX-35) to study the time onset of bone formation by calcein labelling. Images were taken with an exposure time 40-80 ms. The incidence of fluorescent staining in the bone areas was recorded, and the number of fluorescent spots in the samples was counted. A quantitative index ($C_{fluor}$), which roughly indicates the early bone formation chance, was calculated as $$C_{fluor} = \Sigma(spots)_m/(incidence)_m$$

where the pedix 'm' indicates the material considered, i.e. m=(T1050, T1050a, T1125a, TCP negative control).

3.5. Results

Figure 3:
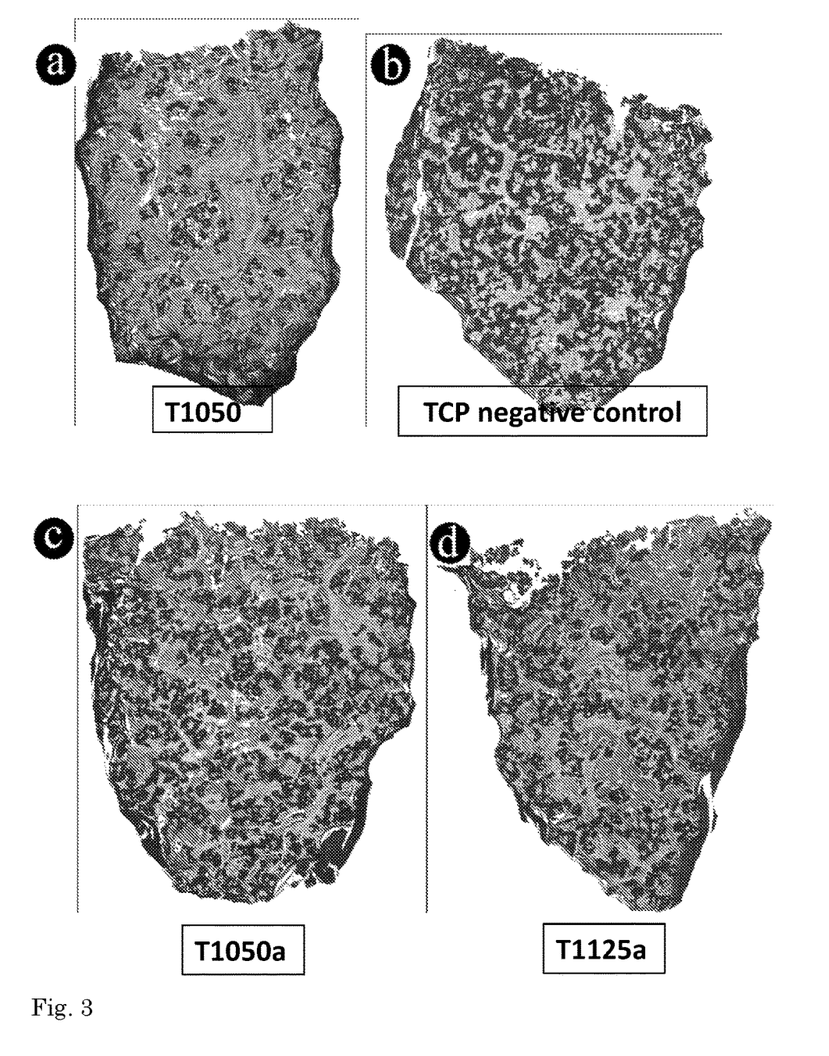
FIG. 3 shows histological overviews of (a) T1050, (b) TCP negative control, (c) T1050a and (d) T1125a. Material is black, bone is stained pink and soft tissues/muscle are stained violet.
Figure 4:
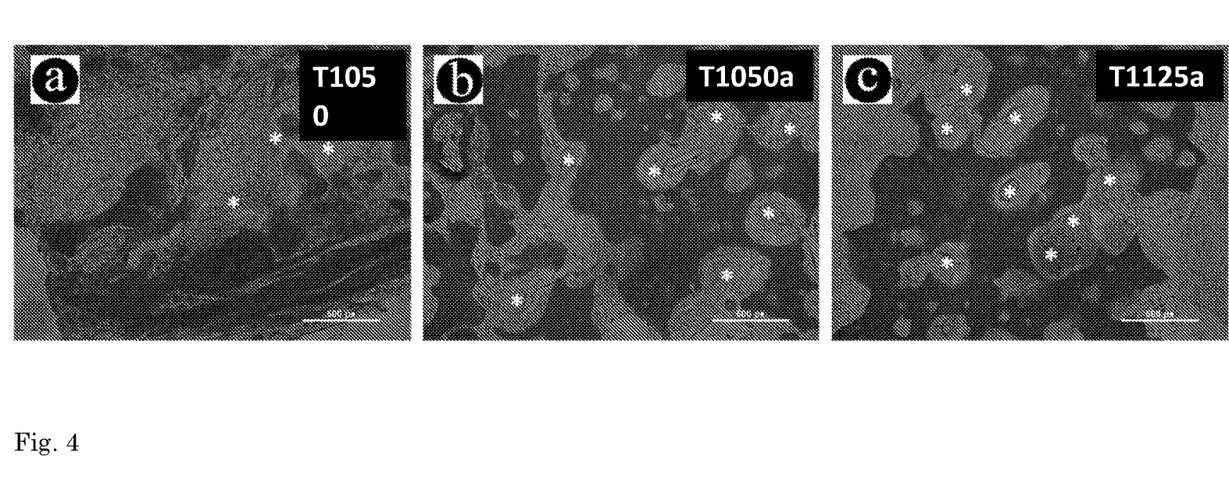
FIG. 4 shows the overlap of fluorescent and light imaging in the same spot of (a) T1050 (prior art material), (b) T1050a (according to the invention) and (c) T1125a (according to the invention). Bright green is calcein staining to bone tissue (indicated by stars). TCP negative control is not shown here as no bone formation occurred.
Figure 5:
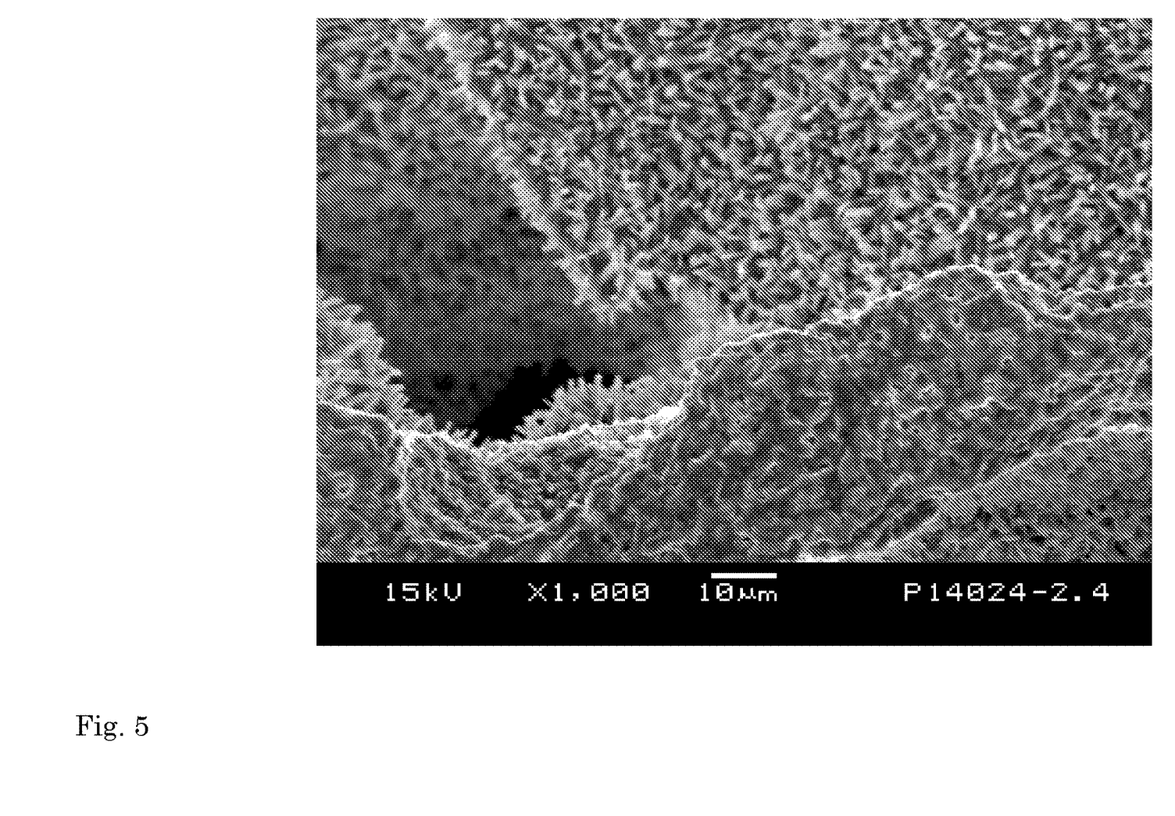
FIG. 5 shows the needle-like surface topography of a material or coating of the invention.
Figure 6:
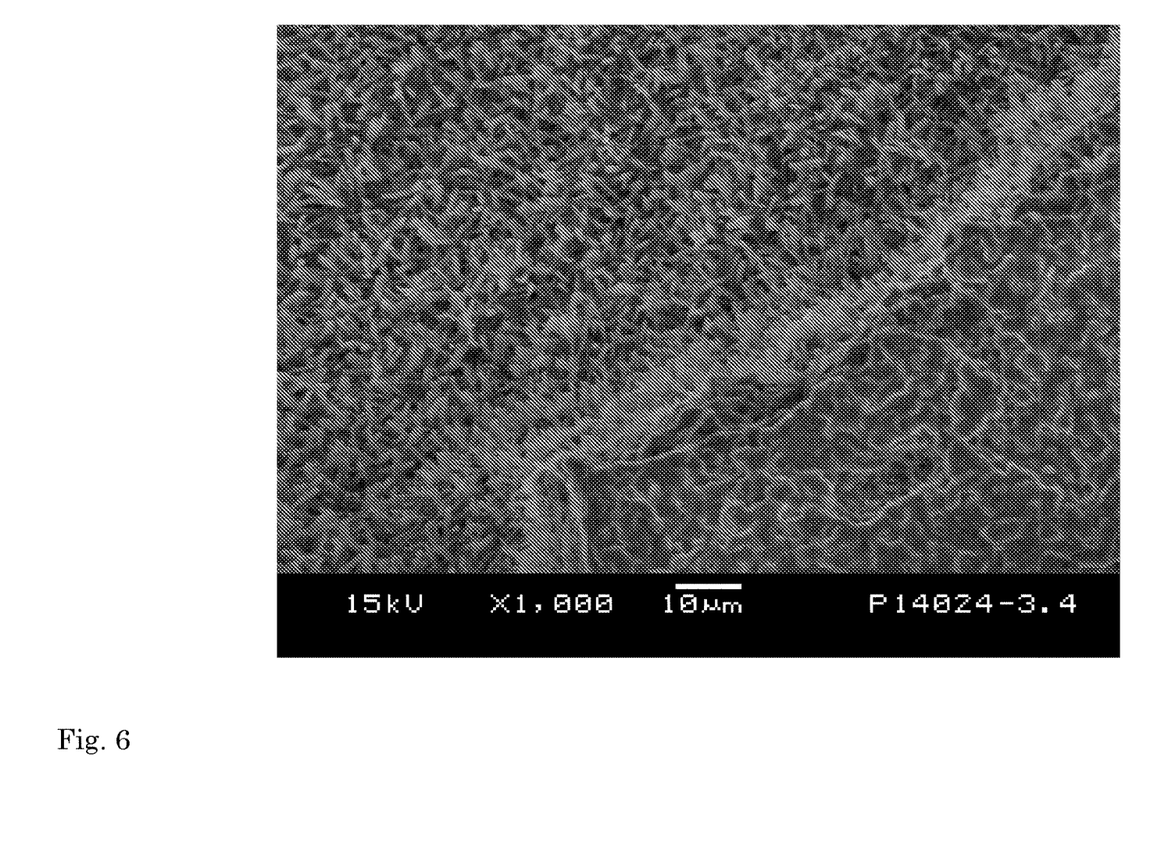
FIG. 6 shows a cross section of a material or coating of the invention. The left-side of the picture clearly shows a needle-like surface topography (the outer layer), whereas the right-side of the picture shows the BCP (inner layer).

A total of eight samples per material were intramuscularly implanted in eight dogs. After 12 weeks eight samples per material were retrieved with their surrounding tissue. No inflammation was seen in any of the explants. Bone formed in T1050, T1050a, T1125a and T1150a implants, but in none of TCP negative control (Table 5, FIG. 3). The quantity of bone formed at 12 weeks was equivalent for T1050, T1050a, T1125a, and significantly more than for T1150. Fluorescent observations on T1050, T1050a and T1125a demonstrated that T1125a could trigger bone formation earlier than six weeks in most explants, while T1050 and T1050a induced bone formation mainly after six weeks (FIG. 4, Table 5). Simultaneously, more bone was formed at week 6 in the autoclaved groups (i.e. T1050a and T1125a) as compared to the control (i.e. T1050) (Table 5). In particular, T1125a showed more bone incidence at week 6 compared to T1050a (Table 5). Histomorphometry results are summarised in Table 5 as well, and indicated that at week 12 no significant differences between hydrothermally treated materials and controls.

3.6. Conclusion

Needle structure (and high surface area) leads to an acceleration in bone formation compared to the classic grain structured calcium phosphate ceramics.

TABLE 5

Overview of the chosen materials for further characterization. $C_{fluor}$ has not been calculated for TCP negative control.

| Material | Bone incidence | Bone [% por.] | Calcein incidence | $\Sigma(spots)_m$ | $C_{fluor}$ |
|---|---|---|---|---|---|
| T1050 | 8/8 | 23 ± 10 | 2/8 | 2 | 1 |
| T1050a | 8/8 | 23.7 ± 10.1 | 4/8 | 12 | 3 |
| T1125a | 8/8 | 22.8 ± 13.3 | 5/8 | 21 | 4.2 |
| T1150a | 4/4 | 2.0 ± 2.0% | NM | NM | NM |
| TCP negative Control | 0/8 | n/a | 0/8 | 0 | n/a |

The invention claimed is:

1. A method for producing an osteoinductive calcium phosphate material, the method comprising the steps of:
   providing a sintered biphasic calcium phosphate (BCP) starting material comprising β-tricalcium phosphate (βTCP) and 4-20 wt. % of hydroxyapatite (HA), the sintered BCP starting material having a surface topography consisting of calcium phosphate grains, and
   subjecting the sintered BCP starting material to hydrothermal treatment at a temperature equal to or higher than 125° C. for a duration sufficient to change calcium phosphate grains on the surface of the starting material into HA needles, to obtain said osteoinductive calcium phosphate material.

2. Method according to claim 1, wherein the sintered BCP starting material has an average grain size in a range of 0.1-3.0 μm.

3. Method according to claim 1, wherein the sintered BCP starting material is porous.

4. Method according to claim 1, wherein the sintered BCP starting material comprises macropores in a size range of 50-1500 μm.

5. Method according to claim 1, wherein the specific surface area of the osteoinductive calcium phosphate material is at least 10-50% higher than that of the BCP starting material.

6. Method according to claim 1, wherein the protein adsorption capacity of the osteoinductive calcium phosphate material is at least 10-50% higher than that of the BCP starting material.

7. Method according to claim 5, wherein the specific surface area of the osteoinductive calcium phosphate material is at least 80-100% higher than that of the sintered BCP starting material.

8. Method according to claim 6, wherein the protein adsorption capacity of the osteoinductive calcium phosphate material is at least 80-100% higher than that of the sintered BCP starting material.

\* \* \* \* \*